United States Patent
Musa (10) Patent No.: US 9,384,990 B2
(45) Date of Patent: Jul. 5, 2016

(54) TITANIUM NITRIDE ELECTRODE

(71) Applicant: IMEC VZW, Leuven (BE)

(72) Inventor: Silke Musa, Leuven (BE)

(73) Assignee: IMEC VZW, Leuven (BE)

(*) Notice: Subject to any disclaimer, the term of this patent is extended or adjusted under 35 U.S.C. 154(b) by 0 days.

(21) Appl. No.: 14/543,107

(22) Filed: Nov. 17, 2014

(65) Prior Publication Data

US 2015/0137275 A1 May 21, 2015

(30) Foreign Application Priority Data

Nov. 21, 2013 (EP) .................................. 13193749

(51) Int. Cl.
| | |
|---|---|
| *H01L 21/44* | (2006.01) |
| *H01L 21/28* | (2006.01) |
| *H01L 21/285* | (2006.01) |
| *H01L 29/45* | (2006.01) |
| *G01N 27/403* | (2006.01) |
| *G01N 27/30* | (2006.01) |
| *H01L 21/00* | (2006.01) |
| *H01L 21/8238* | (2006.01) |

(52) U.S. Cl.
CPC .......... *H01L 21/28506* (2013.01); *G01N 27/30* (2013.01); *G01N 27/403* (2013.01); *H01L 29/45* (2013.01)

(58) Field of Classification Search
None
See application file for complete search history.

(56) References Cited

U.S. PATENT DOCUMENTS 6,899,818 B2 * 5/2005 Schwartzkopf ................ 216/83
2010/0233545 A1 * 9/2010 Sano et al. ................. 429/231.5

FOREIGN PATENT DOCUMENTS

DE        4324185 A1    1/1995

OTHER PUBLICATIONS

European Search Report, European Patent Application No. 13193749.2 dated Feb. 10, 2014.
Korablov, Sergiy et al., Hydrothermal Corrosion of TiN PVD Films on SUS-304, Corrosion Science, vol. 45, No. 3, Mar. 2003, pp. 531-543.
Korablov, Sergiy et al., "Hydrothermal Corrosion of TiA1N and CrN PVD Films on Stainless Steel", Corrosion Science, vol. 47, No. 7, Jul. 2005, pp. 1839-1854.
Kirchner, Carolina Nunes et al., "Evaluation of Thin Film Titanium Nitride Electrodes for Electroanalytical Applications", Electroanalysis, No. vol. 19, No. 10, May 2007, pp. 1023-1031.
Sanchez, G. et al., "Electrical Characterization of Titanium Nitride Surfaces for Pacing Electrodes", Journal of Materials Science, vol. 41, No. 11, Apr. 12, 2006, pp. 3241-3247.

* cited by examiner

*Primary Examiner* — Calvin Choi
(74) *Attorney, Agent, or Firm* — McDonnell Boehnen Hulbert & Berghoff LLP (57) ABSTRACT

The present invention relates to a method for decreasing the impedance of a titanium nitride element for use in an electrode component. The method comprises obtaining a titanium nitride element and hydrothermally treating the titanium nitride element by immersing the titanium nitride element in a liquid comprising water while heating said liquid.

8 Claims, 6 Drawing Sheets

TITANIUM NITRIDE ELECTRODE

CROSS-REFERENCE

This application claims priority from EP 13193749.2, filed Nov. 21, 2013 which is incorporated by references in its entirety.

FIELD OF THE INVENTION

The invention relates to the field of electrodes, e.g. electrodes suitable for biosensors. More specifically it relates to a low-impedance, high-capacitance TiN electrode suitable for biosensor applications and to methods for manufacturing such electrode.

BACKGROUND OF THE INVENTION

Electrodes are important components for biosensor chips, in which they are typically used for transducing biological and/or chemical signals into measurable electrical signals, e.g. voltages or currents. For such biosensor applications, an electrode is preferred that exhibits a good sensitivity, selectivity, and stability for reliably detecting a biological and/or chemical signal over a specific period of time. State-of-the-art biosensors may rely on integrated complementary metal-oxide semiconductor (CMOS) circuitry for local signal conditioning, wireless communication, cell or particle manipulation and/or other optical, electrical and/or mechanical modalities. Therefore, a biosensor electrode is also preferably compatible with back-end-of-line CMOS processing.

Biosensor chips with integrated electrodes may find application in drug discovery pharmacology, neural interface systems, cell-based biosensors and electrophysiology research tools such as multi-electrode arrays. More specifically, implantable neural probes may require dense arrays of small electrodes, e.g. having an area in the range from about 25 $\mu m^2$ to 144 $\mu m^2$, which also have low electrode-tissue interface impedance in order to achieve reliable measurement of small neuronal action potentials at a high spatial resolution.

Similar to conventional capacitors, the electrode-tissue interface impedance is largely electrostatic in nature due to the formation of a space-charge region, e.g. a double-layer capacitance (DLC), at the solid-liquid interface. Hence, the impedance strongly depends on the total accessible external and internal surface area of the electrode, in which the external surface area is defined by the morphology and grain size of the electrode material and the internal surface area is a function of the porosity of the material. The total accessible area also depends on the hydrophilicity of the material, and hence also on the chemical composition of the material surface.

In addition to the electrostatic double-layer capacitance, some electrode materials can exhibit a so-called pseudo-capacitance (PC), in which the capacitive behaviour is not caused by static charge-separation, but by charge-transfer processes at the electrode surface such as electrosorption, e.g. H-atom adsorption on Pt, redox reactions, e.g. fast redox reactions accompanied by (de)protonation at the surface of transition metal oxides comprising multiple oxidation states, and ion intercalation, e.g. Li+-ion intercalation that lead to charge build-up at the electrode-electrolyte interface. Double-layer capacitance and pseudo-capacitance add up to a common capacitance value of an electrode, and both increase with increasing accessible surface area. Unlike the DLC, the PC can also be enhanced by chemically modifying, e.g. functionalizing, the electrode material in order to facilitate charge-transfer processes. For many biosensor applications, it may be desirable to increase the overall capacitance, and hence the accessible surface area, while minimizing the geometric area in order to improve sensitivity and spatial resolution.

Many electrode materials are known in the art which may be suitable for use in biosensors, for example thin-film materials such as Au, Pt, Ir, IrOx, and TiN, conducting polymers such as poly-(3,4-ethylenedioxythiophene) (PEDOT) and polypyrrole, and carbon-based materials such as carbon nanotubes and nanofibres.

Unfortunately, except for Ti and TiN, the above-mentioned materials may be incompatible with the strict contamination rules in standard back-end-of-line (BEOL) CMOS processing, e.g. excluding the use of Au, expensive, e.g. Pt and Ir, and/or difficult to integrate in standard CMOS processing, e.g. conducting polymers and carbon materials. TiN is a standard CMOS material which has for example been used, amongst others, as surface area-enhancing diffusion barrier and anti-reflective coating. It is also relatively cheap to fabricate and has a proven track record as electrode material in cardiac pacemakers due to its good biocompatibility, chemical and mechanical stability, and corrosion resistance. Furthermore, TiN is an excellent moisture barrier and its microcolumnar structure provides a high surface roughness and hence a large accessible surface area. These properties make it a very interesting candidate for integration in biosensor chips.

Commercial chips, such as the multi-electrode arrays distributed by Multichannel Systems, employ TiN as electrode material. For such chips, impedances of less than 1 MOhm may be achieved for 79 $\mu m^2$ electrodes, e.g. using 900 nm thick TiN deposited using plasma-enhanced chemical vapour deposition (PECVD). Generally, increasing the TiN thickness also increases the surface roughness due to the formation of large columnar grains, and therefore also enhances the accessible surface area.

While using a TiN layer having a large thickness is a viable path towards increasing the accessible surface area and hence capacitance of electrodes, its fabrication is not standard in CMOS BEOL-processing, where a thickness of tens to a few hundreds of nm are common Depositing and patterning thick TiN elements may therefore imply a disadvantageously extensive process development and time-consuming hardware maintenance. Consequently, cost-effective approaches towards improving the overall TiN capacitance while minimizing the layer thickness may be preferred.

DE 4324185 discloses a stimulating electrode, for example for a pacemaker, comprising titanium and a porous layer of titanium nitride. The active surface area is increased, according to this disclosure, by introducing microstructures in the surface of the functional electrode member before coating with the porous material.

SUMMARY OF THE INVENTION

It is an object of embodiments of the present invention to provide good impedance and capacitance characteristics in titanium nitride electrodes, e.g. in titanium nitride electrodes suitable for use in biosensors.

Achieving high electrode capacitance and hence low impedance, since the impedance scales inversely with the capacitance, may be important for ensuring the integrity of the transduced signals, which can have very small amplitudes. Hence, amplifiers may be typically required to improve the signal-to-noise ratio. In order for neural amplifiers to operate optimally and prevent signal attenuation due to the voltage divider effect, their input capacitance has to be significantly smaller than the electrode capacitance. Input capacitances of state-of-the-art neural amplifiers are few pF (e.g. 5 pF), which translates into input impedances of few tens of MOhm at 1 kHz (e.g. 31.8 MOhm at 1 kHz). Therefore, electrode capacitances may preferably be at least 2 orders of magnitude larger, e.g. a few hundreds of pF, to keep measured voltage errors for example smaller than 1%. In case of the amplifier example hereinabove, the electrode impedance at 1 kHz has to be about 318 kOhm or smaller.

The above objective is accomplished by a method and device according to the present invention.

In a first aspect, the present invention provides a method for decreasing the impedance of a titanium nitride element for use in an electrode component. The method comprises obtaining a titanium nitride element and hydrothermally treating the titanium nitride element by immersing the titanium nitride element in a heated liquid comprising water. The liquid comprising water (aqueous solution) may be hot before immersing the titanium nitride element, or may be heated once and while the titanium nitride element is immersed therein. In embodiments of the present invention, the method may be applied while maintaining a vapour pressure at or above ambient atmospheric pressure on said liquid.

It is an advantage of embodiments of the present invention that an electrode may be provided in a CMOS-processing compatible manner.

It is an advantage of embodiments of the present invention that a method according to embodiments is relatively simple to implement.

It is an advantage of embodiments of the present invention that a method according to embodiments is cost-effective.

It is an advantage of embodiments of the present invention that a method according to embodiments does not require noble metals.

It is an advantage of embodiments of the present invention that an electrode is provided that is biocompatible, e.g. which is suitable for neural probes.

It is an advantage of embodiments of the present invention that an electrode is provided that is suitable for the use in biosensors, for catalysis, photocatalysis and/or electrocatalysis, for use in lithium batteries, in hydrogen storage, and/or in solar-cell technologies.

In embodiments of the present invention, immersing said titanium nitride element in the liquid comprising water may comprise immersing said titanium nitride element in deionized water.

In alterative embodiments of the present invention, immersing said titanium nitride element in the liquid comprising water may comprise immersing said titanium nitride element in an acidic aqueous solution, for instance in a hydrogen chlorine aqueous solution or in a sulphuric acid aqueous solution, or in an alkaline aqueous solution.

In embodiments of the present invention, heating said liquid may comprise heating said liquid in a closed vessel. Depending on the type of closure of the vessel, vapour pressure may be maintained at or above ambient atmospheric pressure.

In embodiments of the present invention, obtaining the titanium nitride element may comprise obtaining a titanium nitride element comprising a titanium nitride film. Obtaining the titanium nitride element may comprise obtaining a semiconductor chip comprising said titanium nitride element or obtaining a semiconductor wafer comprising said titanium nitride element. Obtaining the semiconductor chip or obtaining the semiconductor wafer may comprise depositing titanium nitride on said semiconductor chip or semiconductor wafer using chemical vapour deposition.

In embodiments of the present invention, hydrothermally treating the titanium nitride element may comprise hydrothermally treating the titanium nitride element for a predetermined time interval, said predetermined time interval for instance being in the range of 30 minutes to 72 hours.

In a second aspect, the present invention provides a semiconductor device comprising an electrode component, the electrode component comprising a titanium nitride element having a surface roughness obtainable by a method according to embodiments of the first aspect of the present invention.

In a third aspect, the present invention provides the use of a method according to any of the embodiments of the first aspect of the present invention for manufacturing a biosensor comprising an electrode component comprising a low-impedance titanium nitride element, for instance a titanium nitride element with an impedance which is decreased by the hydrothermal treatment of embodiments of the first aspect with a factor between 5 and 100.

Particular and preferred aspects of the invention are set out in the accompanying independent and dependent claims. Features from the dependent claims may be combined with features of the independent claims and with features of other dependent claims as appropriate and not merely as explicitly set out in the claims.

These and other aspects of the invention will be apparent from and elucidated with reference to the embodiment(s) described hereinafter.

The drawings are only schematic and are non-limiting. In the drawings, the size of some of the elements may be exaggerated and not drawn on scale for illustrative purposes.

Any reference signs in the claims shall not be construed as limiting the scope.

In the different drawings, the same reference signs refer to the same or analogous elements.

DETAILED DESCRIPTION OF ILLUSTRATIVE EMBODIMENTS

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

Where in embodiments of the present invention reference is made to "hydrothermal treatment," "hydrothermal method" or "hydrothermal synthesis", reference is made to a method for locally leaching and/or re-depositing material from a substrate in a high-temperature aqueous solution. High temperature may refer to a temperature above room temperature, e.g. a temperature of 300 K or higher, preferably a temperature of 320 K or higher, even more preferred a temperature in the range of 330 K to 800 K. Such treatment may be conducted under ambient pressure or under elevated pressure, e.g. a pressure higher than ambient pressure, e.g. higher than 100 kPa, for example 120 kPa, or even higher. Hydrothermal treatment may for example be performed in an autoclave, e.g. in a steel pressure vessel or in a sealed beaker exposed to a heat source. The pressurized vessel or bomb may be heated at a predetermined temperature, while under pressure, for a period in the range from 30 minutes to several days, e.g. 72 hours.

In a first aspect, embodiments of the present invention relate to a method for decreasing the impedance of a titanium nitride element for use in an electrode component. The method comprises obtaining the titanium nitride element and hydrothermally treating the titanium nitride element by immersing the titanium nitride element in a liquid comprising water, while heating the liquid and maintaining a vapour pressure at or above ambient atmospheric pressure on the liquid.

Surprisingly, the hydrothermal treatment of the titanium nitride element may enable crystals to grow on the surface of the titanium nitride element and/or may inhomogeneously etch the surface, such that a porous matrix is left behind. Thus, an increase in the contact surface of the element is achieved, either by such crystal growth, by such inhomogeneous etching or by a combination of both effects.

Figure 1:
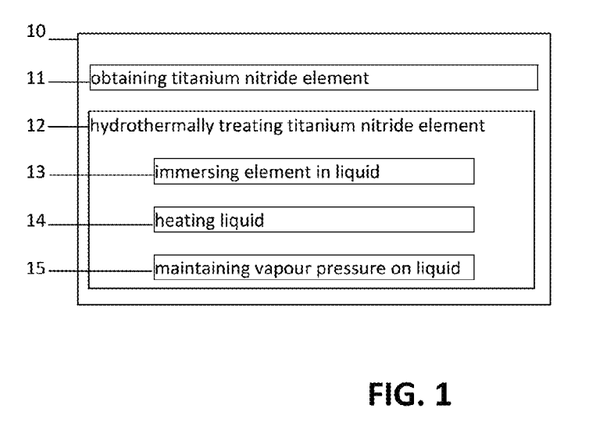
FIG. 1 schematically illustrates a method according to embodiments of the present invention.

Referring to FIG. 1, an exemplary method 10 according to embodiments of the present invention is illustrated. This method 10 for decreasing the impedance of a titanium nitride element for use in an electrode component, may be applied in manufacturing of semiconductor devices, such as biosensors, comprising an electrode component, which comprises the titanium nitride element.

The method 10 comprises obtaining 11 the titanium nitride element. For example, obtaining 11 the titanium nitride element may comprise obtaining a titanium nitride element comprising a titanium nitride film, e.g. the titanium nitride element may be a titanium nitride film suitable for use in an electrode component. Obtaining 11 the titanium nitride element may alternatively also comprise obtaining a semiconductor chip comprising the titanium nitride element or obtaining a semiconductor wafer comprising the titanium nitride element. For example, the semiconductor chip or the semiconductor wafer may be obtained by depositing titanium nitride on this semiconductor chip or wafer. Depositing titanium nitride on the semiconductor chip or wafer may comprise using chemical vapour deposition, such as applying direct current (DC) or radio frequency (RF) plasma enhanced chemical vapour deposition (PECVD) or applying metal organic chemical vapour deposition (MOCVD). Such semiconductor chip may for example be a biosensor or may be intended as a component of a biosensor, having an electrode component comprising the titanium nitride element.

The method 10 comprises hydrothermally treating 12 the titanium nitride element by immersing 13 the titanium nitride element in a liquid comprising water. Hydrothermally treating 12 the titanium nitride element may comprise hydrothermally treating the titanium nitride element for a predetermined time interval, in which this predetermined time interval is in the range of 30 minutes to 72 hours, preferably in the range of 1 hour to 36 hours, or even more preferred, in the range of 1 hour to 6 hours, for example about 2 hours or about 3 hours.

Immersing 13 the titanium nitride element in the liquid comprising water may comprise immersing the titanium nitride element in deionized water. The deionized water may be heated to a temperature in the range of 60° to 100° C., e.g. in the range of 70° C. to 90° C., e.g. to about 80° C. For example, chips with TiN electrodes may be immersed in deionized water at a temperature of 80° C. in a $N_2$ oven, e.g. for about 36 hours.

Immersing 13 the titanium nitride element in the liquid comprising water may comprise immersing the titanium nitride element in an inorganic liquid such as deionized water or an inorganic aqueous solution. The liquid may be pH neutral, acidic or alkaline.

Immersing 13 the titanium nitride element in the liquid comprising water may comprise immersing the titanium nitride element in an acidic aqueous solution, for example, in a hydrogen chlorine (HCl) aqueous solution or in a sulphuric acid ($H_2SO_4$) aqueous solution.

Immersing 13 the titanium nitride element in the liquid comprising water may comprise immersing the titanium nitride element in an alkaline aqueous solution, for example a sodium hydroxide (NaOH) aqueous solution or an ammonium hydroxide ($NH_4OH$) aqueous solution.

In particular embodiments of the present invention, the pH of the aqueous solution is between 0 and 14.

In the method 10, the titanium nitride element is immersed 13 in the liquid comprising water while heating 14 the liquid and maintaining 15 a vapour pressure at or above ambient atmospheric pressure on the liquid. Heating the liquid and maintaining the vapour pressure at or above ambient atmospheric pressure may comprise heating the liquid in a closed vessel, e.g. a beaker closed off with aluminium foil. Heating the liquid and maintaining the vapour pressure at or above ambient atmospheric pressure may comprise heating the liquid in a thermostatic oven, e.g. an $N_2$ oven.

In a second aspect, embodiments of the present invention also relate to a semiconductor device comprising an electrode component, in which the electrode component comprises a titanium nitride element which has a surface roughness obtained by a method according to the first aspect of the present invention.

Embodiments of the present invention also relate to the use of a method according to embodiments of the first aspect of the present invention for manufacturing a biosensor comprising an electrode component comprising a low-impedance titanium nitride element, for example having an impedance at 1 MHz smaller than or equal to 1 MOhm, and preferably less than 500 kOhm, such as 318 kOhm, or even more preferred, smaller than or equal to 300 kOhm. For example, embodiments of the present invention also relate to a method for manufacturing a biosensor comprising an electrode component, in which such method for manufacturing comprises decreasing the impedance of a titanium nitride element for use in the electrode component by a method according to the first aspect of the present invention. Similarly, embodiments of the present invention may also relate to the use of a method according to embodiments of the first aspect of the present invention for manufacturing a photovoltaic cell or a battery cell comprising an electrode component comprising a titanium nitride element having an advantageous surface roughness.

Embodiments of the present invention also relate to the use of a method according to embodiments of the first aspect of the present invention for manufacturing a biosensor comprising an electrode component comprising a titanium nitride element, for example, the use of such method for lowering the impedance of the titanium nitride element by at least a factor of 5, e.g. by at least a factor of 20, e.g. by a factor in the range of 5 to 100.

During a hydrothermal treatment according to embodiments of the present invention, nanoneedles, nanorods and/or nanocrystals, may form at the titanium nitride surface and/or nanopores may form in the titanium nitride layer, which may advantageously increase its surface area. This may therefore also advantageously increase the double layer capacitance and/or the pseudo-capacitance of the titanium nitride element. Similarly, the chemical composition of the titanium nitride electrode may be changed, e.g. oxidized, thus advantageously further increasing the pseudo-capacitance.

Several examples of embodiments of the present invention will be provided hereinbelow.

In the first two examples, acidic hydrothermal treatment of titanium nitride was performed in solutions of respectively 0.01 M (first example) and 1 M $H_2SO_4$ (second example). In each case, the solutions were prepared and heated to 80° C. on hotplates under magnetic stirring. In an alternative approach, beakers with the solutions can be placed in an oven at 80° C. Chips with TiN electrodes were then immersed in these solutions for up to 36 hours. During immersion, the beakers holding the solutions were sealed with Al foil. At the end of the hydrothermal treatment, the chips were removed and thoroughly rinsed with deionized water.

The TiN electrode impedance was measured in aqueous phosphate buffered saline (0.15 M NaCl, pH 7.4) before and after the hydrothermal treatment. Up to five different TiN deposition tools using different deposition techniques, namely direct current plasma enhanced chemical vapour deposition (DC PECVD), radio frequency plasma enhanced chemical vapour deposition (RF PECVD) and metal organic chemical vapour deposition (MOCVD), and different settings were evaluated. The nominal TiN thickness was either 100, 300, or 600 nm. Hereinbelow, tool A, D and E refer to different DC PECVD tools, tool C refers to a RF PECVD and tool B to a MOCVD tool.

Figure 2:
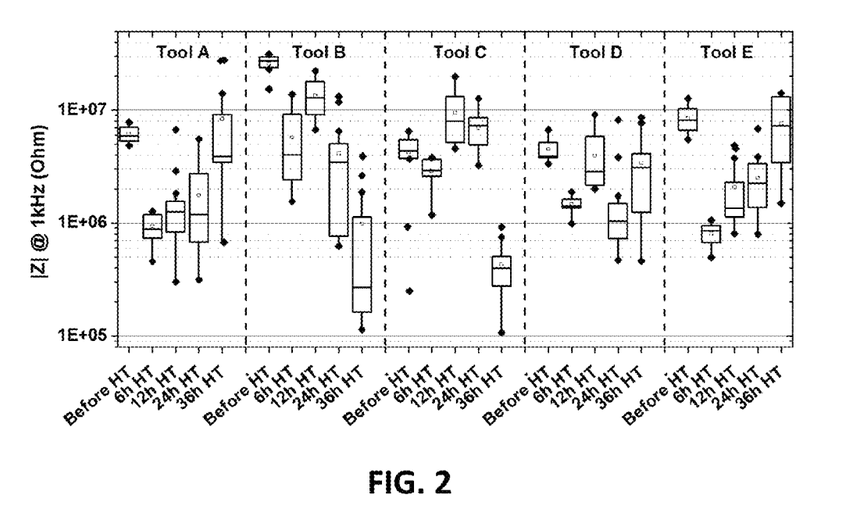
FIG. 2 illustrates the effect of different durations of hydrothermal treatment (HT) in 0.01 M $H_2SO_4$ according to a first example of the present invention on the TiN electrode impedance where TiN is deposited by different deposition techniques.

FIG. 2 shows the effect of the hydrothermal treatment on the electrode's impedance. Box plots of electrode impedances |Z| are shown which were measured for an alternating current (AC) frequency of 1 kHz. The five different TiN deposition tools, referred to as tool A to E, were investigated. Nominal TiN thickness was 100 nm. For each tool, 1 chip with 13 electrodes of 154 µm² was measured in phosphate buffered saline (PBS) before applying the hydrothermal treatment. The chips were then immersed in a beaker with 0.01 M $H_2SO_4$ at a temperature of 80° C. on a hotplate with magnetic stirring. After respectively 6 hours (for tool A and E), 12 hours (for tool B and C) and 24 hours (for tool D) of total accumulated hydrothermal treatment time, the chips were removed, cleaned with deionized water, measured in PBS, and re-immersed in the hot $H_2SO_4$. A final measurement was performed after 36 hours of total hydrothermal treatment time.

In this example, the lowest average impedances and data variations were achieved after 6 hours of hydrothermal treatment for tool A and E, after 36 hours for tool B and C, and after 24 hours for tool D. For tool B, the average impedance dropped maximally by a factor of about 30, while for the other tools, the impedance dropped maximally by a factor in the range of 5 to 10.

Figure 3:
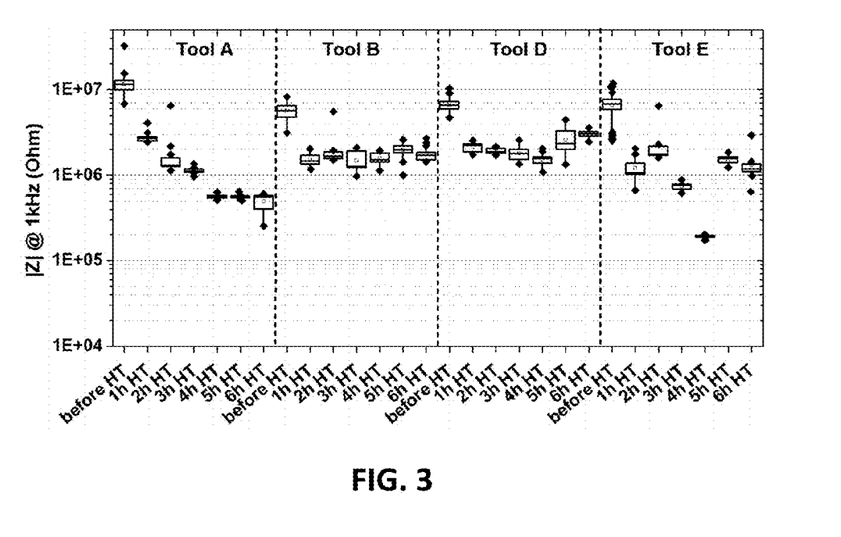
FIG. 3 illustrates the impedance drop during the initial 6 hours of hydrothermal treatment in 0.01 M $H_2SO_4$ according to a second example for TiN deposited by different deposition techniques.

To illustrate the impedance drop after the initial 6 hours of hydrothermal treatment in more detail, in a further example, 6 chips per tool were measured before hydrothermal treatment and after every hour of hydrothermal treatment in 0.01 M $H_2SO_4$ at 80 ° C., e.g. for a maximum of 6 hours. FIG. 3 shows box plots of electrode impedances, in units of Ohm, measured at 1 kHz. Four different TiN deposition tools, tools A, B, D and E, were used, excluding tool C for this example. Nominal TiN thickness was 100 nm. For each tool, 6 chips with 13 electrodes of 154 µm² were measured in PBS before hydrothermal treatment. The chips were then immersed in a beaker with 0.01 M $H_2SO_4$ at 80° C. on a hotplate with magnetic stirring. After each hour of hydrothermal treatment, one chip per tool was removed, cleaned with deionized water, and measured in PBS. The last chip was removed and measured after 6 hours of hydrothermal treatment. The box plots labelled as "before HT" represent data from all 6 chips of a respective tool.

Similar to the exemplary results shown in FIG. 2, the lowest average impedances after 6 hours of hydrothermal treatment HT could be achieved with TiN electrodes which were deposited using tools A and E. The largest impedance drop, of about a factor 20, was observed for tool A after 6 hours of hydrothermal treatment. For the other tools, the largest impedance drop was observed after a hydrothermal treatment time of 3 hours for tool B (achieving a factor of about 5), 4 hours for tool D (achieving a factor of about 5) and 3 hours for tool E (achieving a factor of about 10). Moreover, only for tool A did an increase in hydrothermal treatment time have a clear effect on the impedance drop, namely a gradual decrease of impedance as function of an increasing treatment time. For the other tools, the impedance seemed to stabilize after 1 hour of hydrothermal treatment.

In a next example, the influence of increased $H_2SO_4$ concentration on the impedance drop is discussed. Here, 6 chips per tool were measured before the hydrothermal treatment and after every hour of treatment in 80° C. 1 M $H_2SO_4$, thus for a maximum of 6 hours.

Figure 4:
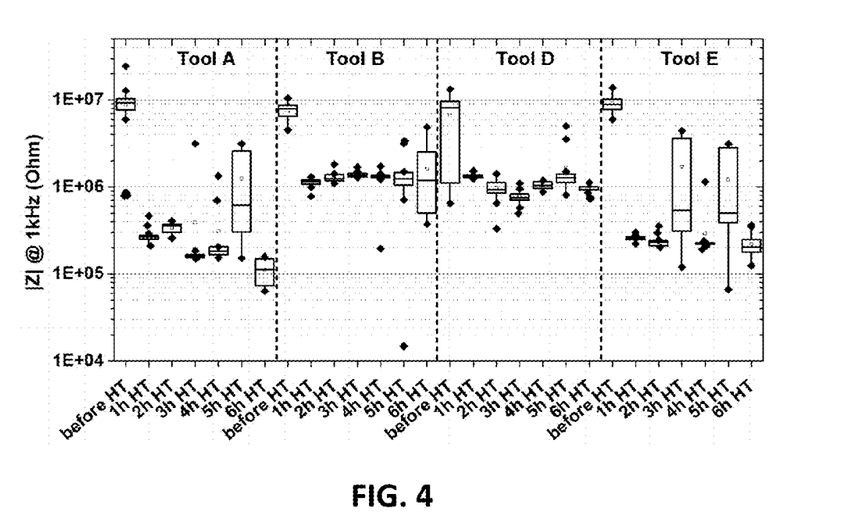
FIG. 4 illustrates, for a third example, the impedance drop during the initial 6 hours of hydrothermal treatment in 1 M $H_2SO_4$.

FIG. 4 shows box plots of electrode impedances measured at 1 kHz (in units of Ohm). Four different TiN deposition tools (A, B, D, E) were used. Nominal TiN thickness was 100 nm. For each tool, 6 chips with 13 electrodes of 154 µm² were measured in PBS before hydrothermal treatment. The chips were then immersed in a beaker with 80° C. hot 1 M $H_2SO_4$ on a hotplate with magnetic stirring. After each hour of hydrothermal treatment, one chip per tool was removed, cleaned with deionized water, and measured in PBS. The last chips were measured after 6 hours of treatment. The box plots labelled as "before HT" represent data from all 6 chips processed with the respective tool.

In this example, the largest average impedance drop was achieved for the chip processed by tool A, achieving an impedance drop factor of about 100 after 6 hours of hydrothermal treatment. For tool B, the largest impedance drop factor of about 7 was obtained after 6 hours hydrothermal treatment, while for tool D a factor of about 10 after 3 hours, and for tool E a factor of about 40 after 6 hours of hydrothermal treatment was obtained. Overall, only the chips processed in tools A and E showed a larger impedance drop after increasing the $H_2SO_4$ concentration from 0.01 M to 1 M. Furthermore, even larger impedance drops may be achievable by further increasing the $H_2SO_4$ concentration for these tools.

In another example, the impact of the TiN thickness on the impedance drop after hydrothermal treatment was investigated. Two different TiN thicknesses, 100 and 600 nm from deposition tool E, were investigated. The hydrothermal treatment was performed for 6 hours in a beaker with 80° C. hot 1 M $H_2SO_4$ on a hotplate under magnetic stirring. For each TiN thickness, 5 chips with 13 electrodes of 154 µm² were measured in PBS before and after the hydrothermal treatment.

Figure 5:
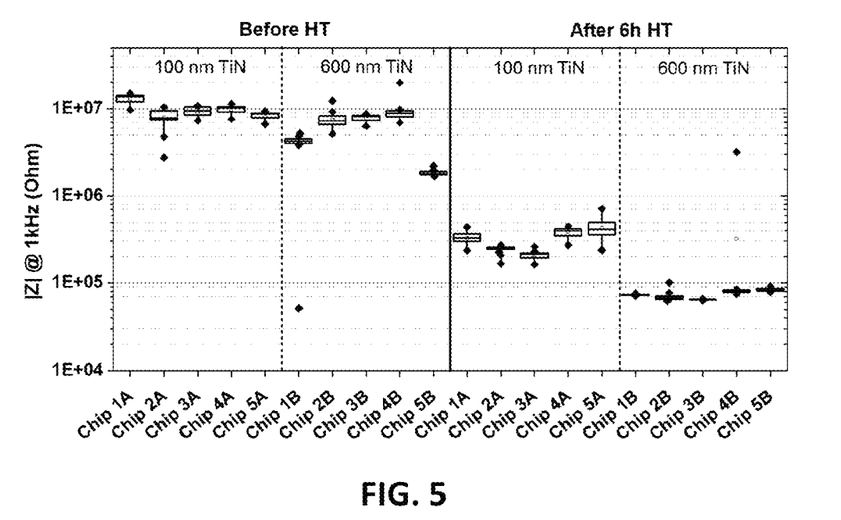
FIG. 5 illustrates, for a fourth example, the effect of TiN thickness on the impedance drop after 6 hours of hydrothermal treatment in 1 M $H_2SO_4$.

FIG. 5 shows box plots of electrode impedances measured at 1 kHz (in units of Ohm). In this example, the largest impedance drop after the hydrothermal treatment was observed for 600 nm thick TiN. For all measured chips with 600 nm thick TiN, the impedance dropped by a factor of approximately 100 compared to the values before the hydrothermal treatment.

Figure 6:
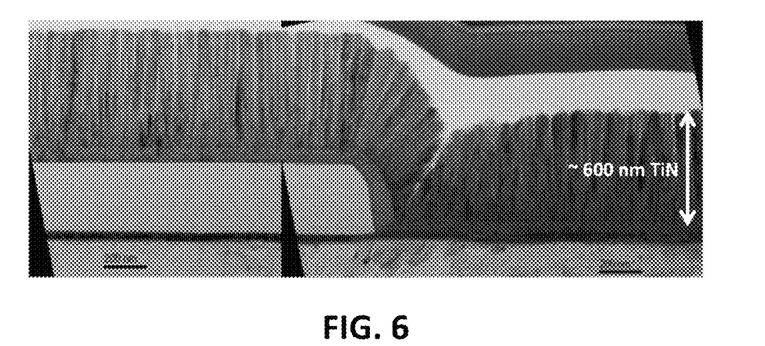
FIG. 6 illustrates, for the fourth example, a TEM cross-sectional image of a 600 nm thick TiN electrode before the hydrothermal treatment.
Figure 7:
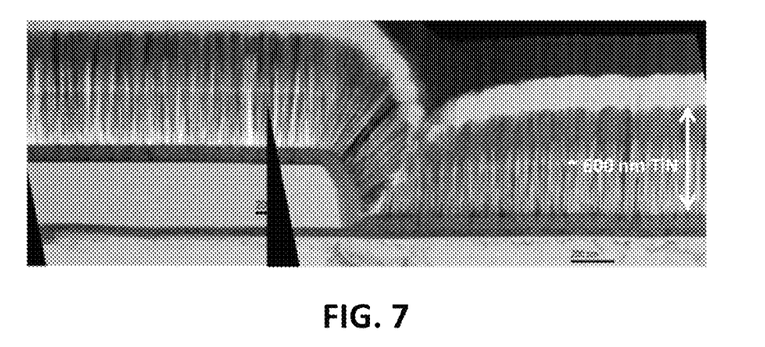
FIG. 7 illustrates, for the fourth example, a TEM cross-sectional image of a 600 nm thick TiN electrode after 6 hours of hydrothermal treatment.

FIGS. 6 and 7 show TEM cross-sectional images before and after hydrothermal treatment of 600 nm thick TiN electrodes deposited in tool E. The hydrothermal treatment was performed for 6 hours in a beaker with 80° C. hot 1 M $H_2SO_4$ on a hotplate under magnetic stirring. According to the TEM analysis, the bottom part of the TiN layer exhibits a more oxidised (brighter), less dense, and more porous morphology compared to the top part after the hydrothermal treatment. This analysis suggests that the impedance drop after the hydrothermal treatment may be correlated with the observed morphological changes, in particular the increased porosity, and hence increased internal surface area.

Figure 8:
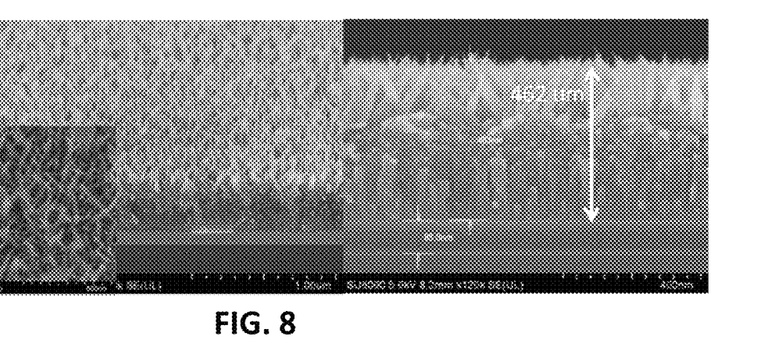
FIG. 8 illustrates, for a fifth example, SEM images of a blanket TiN film with an initial thickness of 300 nm after hydrothermal treatment for 36 h in 80° C. hot 0.01 M $H_2SO_4$.

Another typical morphological change of TiN after hydrothermal treatment is illustrated in FIG. 8. In this example, a 300 nm thick TiN layer was immersed in 80° C. hot 0.01 M $H_2SO_4$ in an $N_2$ oven without magnetic stirring for 36 hours. The hydrothermal treatment was performed in a glass beaker sealed with Al foil. After the hydrothermal treatment, nanorods having a length of about 200 nm were observed on the TiN surface. Such nanorods may significantly increase the TiN surface and thus advantageously reduce the electrode impedance.

Typically, biosensor applications including neural probes require electrodes with stable impedances over prolonged storage and usage periods. In the following 2 examples, the impedances of chips stored in air and PBS for 8 weeks are shown in FIG. 9, and FIG. 10, respectively.

Figure 9:
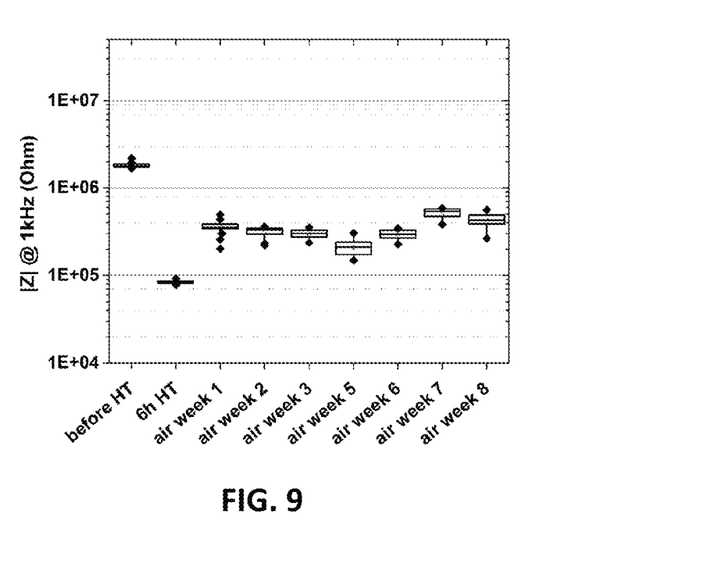
FIG. 9 illustrates the long-term stability of TiN electrode impedances after hydrothermal treatment and storage in air according to the fourth example of the present invention.

FIG. 9 shows the long-term stability of electrode impedances after hydrothermal treatment and storage in air. The box plots shown in FIG. 6 illustrate electrode impedances in Ohm measured at 1 kHz. The nominal TiN thickness was 600 nm deposited in tool E. One chip with 13 electrodes of 154 µm² was measured in PBS before hydrothermal treatment and after 6 hours of hydrothermal treatment in 1 M $H_2SO_4$ at 80°

C. on a hotplate with magnetic stirring. The chip was then stored in air, and the electrode impedance was monitored weekly for 8 weeks. After 1 week in air, the electrode impedance increased by a factor of about 5 compared to the value after 6 hours of hydrothermal treatment and remained relatively stable thereafter.

Figure 10:
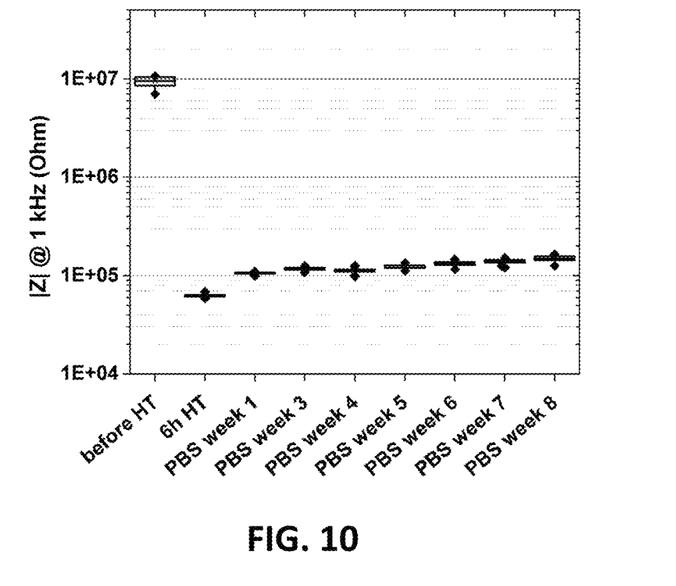
FIG. 10 illustrates the long-term stability of TiN electrode impedances after hydrothermal treatment and storage in PBS according to the fourth example of the present invention.

FIG. 10 illustrates the long-term stability of electrode impedances after hydrothermal treatment and storage in PBS. Illustrated are box plots of electrode impedances measured at 1 kHz, in Ohm. Nominal TiN thickness was 600 nm deposited in tool E. One chip with 13 electrodes of 154 μm² was measured in PBS before hydrothermal treatment and after 6 hours of hydrothermal treatment in 1 M $H_2SO_4$ at 80° C. on a hotplate with magnetic stirring. The chip was then stored in PBS for 8 weeks, and the electrode impedance was monitored weekly. A gradual impedance increase by a factor of 2 compared to the value after HT was observed.

In yet another example, acidic hydrothermal treatment in HCl is presented. A solution of 18% HCl was prepared and heated to 60° C. on a hotplate under magnetic stirring. Chips with TiN electrodes were immersed in the solution for up to 3 hours while keeping the beakers closed with a plastic lid. At the end of the hydrothermal treatment, the chips were removed and thoroughly rinsed with deionized water. The TiN electrode impedance was measured in aqueous phosphate buffered saline (PBS, 0.15 M NaCl, pH 7.4) before and after the treatment.

Figure 11:
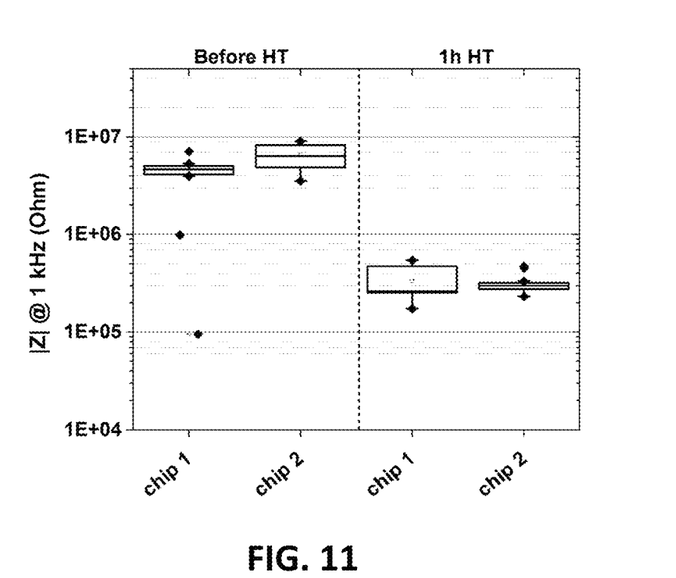
FIG. 11 illustrates the effect of hydrothermal treatment (HT) in aqueous HCl according to a sixth example of the present invention on the TiN electrode impedance.

FIG. 11 illustrates the effect of the hydrothermal treatment on the electrode impedance. Shown are box plots for electrode impedances measured at 1 kHz, in Ohm. Nominal TiN thickness was 100 nm deposited in tool A. Two chips with 13 electrodes of 154 μm² were measured in PBS before the hydrothermal treatment. The chips were then immersed in a beaker with 18% HCl at 60° C. on a hotplate with magnetic stirring. After 1 hour of HT, the chips were removed, cleaned with deionized water, and again measured in PBS. For both chips, the average impedance after 1 hour of HT dropped by a factor of approximately 17.

In a last example, hydrothermal treatment in deionized water is presented. A beaker with deionized water was heated to 80° C. in an $N_2$ oven. Chips with TiN electrodes were immersed in the solution for up to 36 hours while keeping the beaker closed with Al foil.

Figure 12:
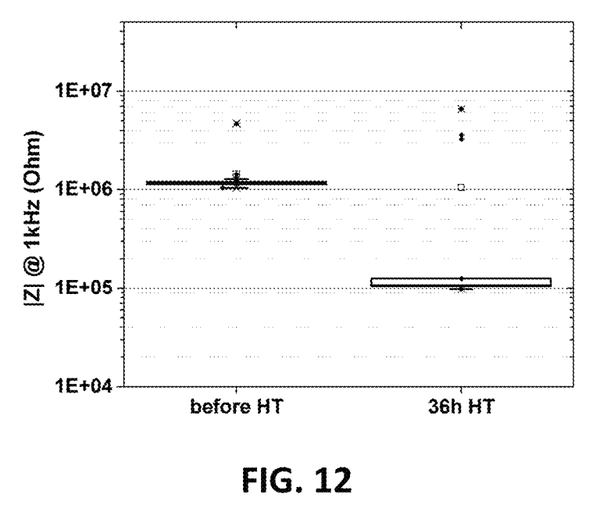
FIG. 12 illustrates the effect of hydrothermal treatment with deionized water according to a seventh example of the present invention on the TiN electrode impedance.

FIG. 12 shows the effect of hydrothermal treatment on electrode impedance for this example. Shown are box plots for electrode impedances measured at 1 kHz in Ohm. The TiN deposition tool previously referred to as tool E was used, and the nominal TiN thickness was 300 nm. The electrode impedance of one chip with 14 electrodes of 660 μm² was measured in PBS before the treatment and after 36 hours of hydrothermal treatment in deionized water. After the hydrothermal treatment, the average electrode impedance was reduced by a factor of approximately 10.

The invention claimed is:

1. A method for decreasing the impedance of a titanium nitride element for use in an electrode component, the method comprising:
   obtaining a titanium nitride element; and
   hydrothermally treating the titanium nitride element by immersing the titanium nitride element in an acidic aqueous solution or an alkaline aqueous solution while heating said aqueous solution for a predetermined time,
   wherein impedance of the titanium nitride element is decreased by a factor between 5 and 100 following the hydrothermal treatment,
   wherein the acidic aqueous solution is selected from a hydrogen chloride aqueous solution and a sulphuric acid aqueous solution, and
   wherein the alkaline aqueous solution is selected from a sodium hydroxide aqueous solution and an ammonium hydroxide aqueous solution.

2. The method according to claim 1, wherein said heating said liquid comprises heating said liquid in a closed vessel.

3. The method according to claim 1, in which obtaining the titanium nitride element comprises obtaining the titanium nitride element comprising a titanium nitride film.

4. The method according to claim 1, in which obtaining the titanium nitride element comprises obtaining a semiconductor chip comprising said titanium nitride element or obtaining a semiconductor wafer comprising said titanium nitride element.

5. The method according to claim 4, in which obtaining the semiconductor chip or obtaining the semiconductor wafer comprises depositing titanium nitride on said semiconductor chip or semiconductor wafer using chemical vapour deposition.

6. The method according to claim 1, in which hydrothermally treating the titanium nitride element comprises hydrothermally treating the titanium nitride element for a predetermined time interval, said predetermined time interval being in the range of 30 minutes to 72 hours.

7. A semiconductor device comprising an electrode component, the electrode component comprising a titanium nitride element having a surface roughness obtainable by a method of claim 1.

8. A biosensor comprising an electrode component comprising a low-impedance titanium nitride element prepared by the method of claim 1.

* * * * *